(12) United States Patent
Davies et al.

(10) Patent No.: US 9,026,384 B2
(45) Date of Patent: May 5, 2015

(54) APPARATUS AND METHOD OF ASSESSING A NARROWING IN A FLUID FILLED TUBE

(75) Inventors: Helen Davies, London (GB); Justin Davies, London (GB)

(73) Assignees: Medsolve Ltd., London, England (GB); Imperial College of Science, Technology and Medicine, London, England (GB)

( * ) Notice: Subject to any disclaimer, the term of this patent is extended or adjusted under 35 U.S.C. 154(b) by 511 days.

(21) Appl. No.: 13/345,495

(22) Filed: Jan. 6, 2012

(65) Prior Publication Data
US 2012/0278008 A1   Nov. 1, 2012

(51) Int. Cl.
*G06F 17/00* (2006.01)
*A61B 5/02* (2006.01)
*A61B 5/0215* (2006.01)
*A61B 5/103* (2006.01)
*G06F 11/30* (2006.01)

(52) U.S. Cl.
CPC .......... *A61B 5/02007* (2013.01); *A61B 5/0215* (2013.01); *A61B 5/103* (2013.01)

(58) Field of Classification Search
CPC ......... G01F 1/86; G01N 9/36; A61B 5/02007
USPC .................... 702/50–52, 182–189
See application file for complete search history.

(56) References Cited

U.S. PATENT DOCUMENTS

| | | | |
|---|---|---|---|
| 6,354,999 B1 | 3/2002 | Dgany et al. | |
| 2003/0204160 A1* | 10/2003 | Kamm et al. | 604/8 |
| 2010/0234698 A1 | 9/2010 | Manstrom et al. | |

FOREIGN PATENT DOCUMENTS

| | | | | |
|---|---|---|---|---|
| EP | 2298162 A1 | 3/2011 | | |
| WO | WO 2010103277 A1 * | 9/2010 | ............. | A61B 5/021 |

OTHER PUBLICATIONS

International Searching Authority/European Patent Office, "International Search Report and the Written Opinion of the International Searching Authority," for PCT/GB2012/050024, mailed Apr. 19, 2012, 14 pages.
Korean Office Action mailed Aug. 21, 2014 in Korean Patent Application No. 2013-7020712, filed Jan. 6, 2012.

* cited by examiner

*Primary Examiner* — Phuong Huynh
(74) *Attorney, Agent, or Firm* — Haynes and Boone, LLP

(57) ABSTRACT

An apparatus and method of assessing a narrowing in a fluid filled tube having a fluid flow pressure wave having a backward-originating pressure component and a forward-originating pressure component without taking a flow velocity measurement, comprising: taking pressure measurements in the tube; separating the pressure components into the backward-originating pressure component and the forward-originating pressure component; identifying a time window when the differential of flow velocity (dU) is minimal or absent; and deriving the backward and forward pressure components for pressure measurements taken in at least the time window.

19 Claims, 3 Drawing Sheets

APPARATUS AND METHOD OF ASSESSING A NARROWING IN A FLUID FILLED TUBE

CROSS-REFERENCE TO RELATED APPLICATION

This application claims priority to United Kingdom Patent Application No. GB1100137.7, filed Jan. 6, 2011, the disclosure of which is incorporated herein by reference in its entirety.

FIELD OF THE INVENTION

This invention relates to an apparatus and method of assessing a narrowing in a fluid filled tube.

BACKGROUND TO THE INVENTION

A fluid filled tube or vessel formed with a constriction or narrowing can be analysed to measure the magnitude of the constriction or narrowing.

An example of a fluid filled tube or vessel formed with a constriction or narrowing is a blood vessel having a stenosis. Assessment or measurement of the constriction can result in a useful parameter to gauge the extent of the constriction.

A standard methodology for assessment of a constriction in a fluid filled tube such as a coronary stenosis is fractional flow reserve (FFR). This technique measures the drop in pressure at two points along a vessel; see FIG. 1 of the accompanying drawings, under conditions of maximal achievable hyperaemia in a coronary environment. The Pd measurement comes from a pressure sensor on the wire and the Pa measurement comes from the catheter. A comparison is then made by expressing the mean distal pressure (Pd), as a proportion of mean proximal pressure (Pa), wherein the values are mean Pa and Pd over the entire cardiac cycle, taken over at least one complete cardiac cycle (but usually an average of 3 or more beats):

$$\text{Fractional Flow Reserve } (FFR) = \frac{P_d}{P_a}$$

Conditions of maximal hyperaemia are usually only achievable by administration of potent vasodilators such as adenosine or dipyridamole. Such vasodilators are necessary to minimise resistance from the distal vascular bed to accurately estimate the drop in pressure across a stenosis. It would be preferable not to have to use vasodilators.

Distal pressure arises from resistance of the microcirculation, in addition to active compression of small microcirculatory vessels which permeate the myocardium. When flow is measured simultaneously at different sites, it is possible to separate the pressure components arising from the distal myocardium (backward-originating pressure), from those arising from the proximal end (forward-originating pressure), $$dP_+ = \frac{1}{2(dP + \rho c\, dU)}$$

$$dP_- = \frac{1}{2(dP - \rho c\, dU)}$$

where dP is the differential of pressure, ρ=density of blood, c=wave speed, and dU is the differential of flow velocity.

$P_+$ isolates forward originating pressure by removing the backward-originating component, and therefore negates the need for administration of vasoactive agents such as adenosine. Thus by comparing the ratio of $P_+$ on either side of a stenosis it is possible to estimate stenosis severity without requiring maximal hyperaemia to be achieved. The isolated forward pressure ratio is expressed as:

$$\text{Forward pressure ratio} = \frac{P_{+\,distal}}{P_{+\,proximal}}$$

Whilst the forward pressure ratio offers a considerable step forward as administration of vasodilator compounds are not required, it requires flow velocity to be measured in addition to pressure. This requires considerable extra skill, additional hardware and added expense.

It is an object of the invention to provide an apparatus and method of assessing a narrowing in a fluid filled tube which does not require a measurement of flow velocity, fluid flow rate, in addition to pressure measurement.

One aspect of the present invention provides a method of assessing a narrowing in a fluid filled tube having a fluid flow pressure wave having a backward-originating pressure component and a forward-originating pressure component without taking a flow velocity measurement, comprising: taking pressure measurements in the tube; separating the pressure components into the backward-originating pressure component and the forward-originating pressure component; identifying a time window when the differential of flow velocity (dU) is minimal or absent; and deriving the backward and forward pressure components for pressure measurements taken in at least the time window.

Another aspect of the present invention provides an apparatus to assess a narrowing in a fluid filled tube having a fluid flow pressure wave having a backward-originating pressure component and a forward-originating pressure component without taking a flow velocity measurement, the apparatus comprising: a pressure measurement device operable to take pressure measurements in the tube; and a processor operable to separate the pressure components into the backward-originating pressure component and the forward-originating pressure component; identify a time window when the differential of flow velocity (dU) is minimal or absent; and to derive the backward and forward pressure components for pressure measurements taken in at least the time window.

A further aspect of the present invention provides a processor configured to assess a narrowing in a fluid filled tube having a fluid flow pressure wave having a backward-originating pressure component and a forward-originating pressure component without taking a flow velocity measurement, the processor: analysing pressure measurements taken in a tube; separating the pressure components into the backward-originating pressure component and the forward-originating pressure component; identifying a time window when the differential of flow velocity (dU) is minimal or absent; and deriving the backward and forward pressure components for pressure measurements taken in at least the time window.

A yet further aspect of the present invention provides a data storage medium carrying a computer program to assess a narrowing in a fluid filled tube having a fluid flow pressure wave having a backward-originating pressure component and a forward-originating pressure component without taking a flow velocity measurement, the program: analysing pressure measurements taken in a tube; separating the pressure components into the backward-originating pressure component and the forward-originating pressure component; identifying a time window when the differential of flow velocity (dU) is minimal or absent; and deriving the backward and forward pressure components for pressure measurements taken in at least the time window.

BRIEF DESCRIPTION OF THE DRAWINGS

In order that the present invention may be more readily understood, embodiments of the invention will now be described with reference to the accompanying drawings, in which.

DESCRIPTION

This invention provides an apparatus and method of assessing a narrowing in a fluid filled tube by measuring the pressure in the tube and does not require a measurement of flow velocity, fluid flow rate, in addition to the pressure measurement.

In a fluid flow system, the separated pressures are given as:

$$dP_+ = \frac{1}{2(dP + \rho c\, dU)}$$

$$dP_- = \frac{1}{2(dP - \rho c\, dU)}$$

where dP is the differential of pressure, ρ=density of blood, c=wave speed, and dU is the differential of flow velocity. The isolated pressure ratio, comparing the ratio of $P_+$ or $P_-$ on either side of a constriction provides a measure, estimate or indication of the severity of the constriction.

The isolated forward pressure ratio using separated pressures is thus:

$$\frac{P_{+\,distal}}{P_{+\,proximal}}$$

Or isolated backward pressure ratio, $$\frac{P_{-\,distal}}{P_{-\,proximal}}$$

Calculating the isolated pressure ratio using this technique gives a pressure only assessment of the severity of the constriction.

Figure 1:
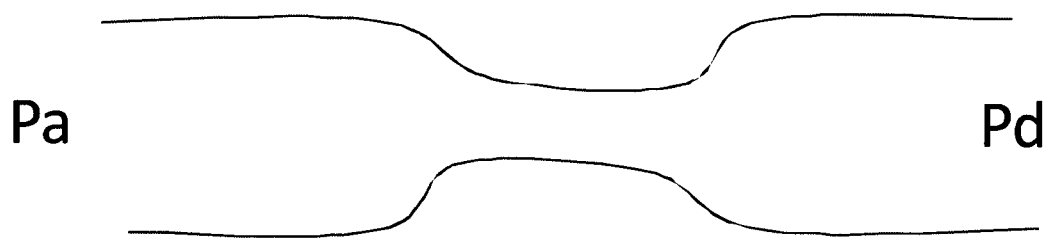
FIG. 1 is a schematic diagram of a tube formed with a constriction with proximal (Pa) and distal (Pd) pressure measurement sites.
Figure 2:
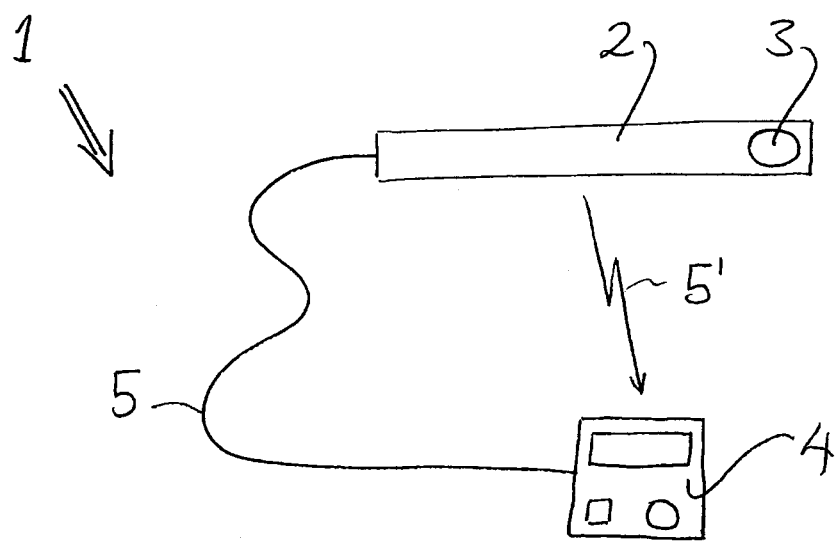
FIG. 2 is a schematic not-to-scale diagram of an apparatus embodying the present invention.
Figure 3:
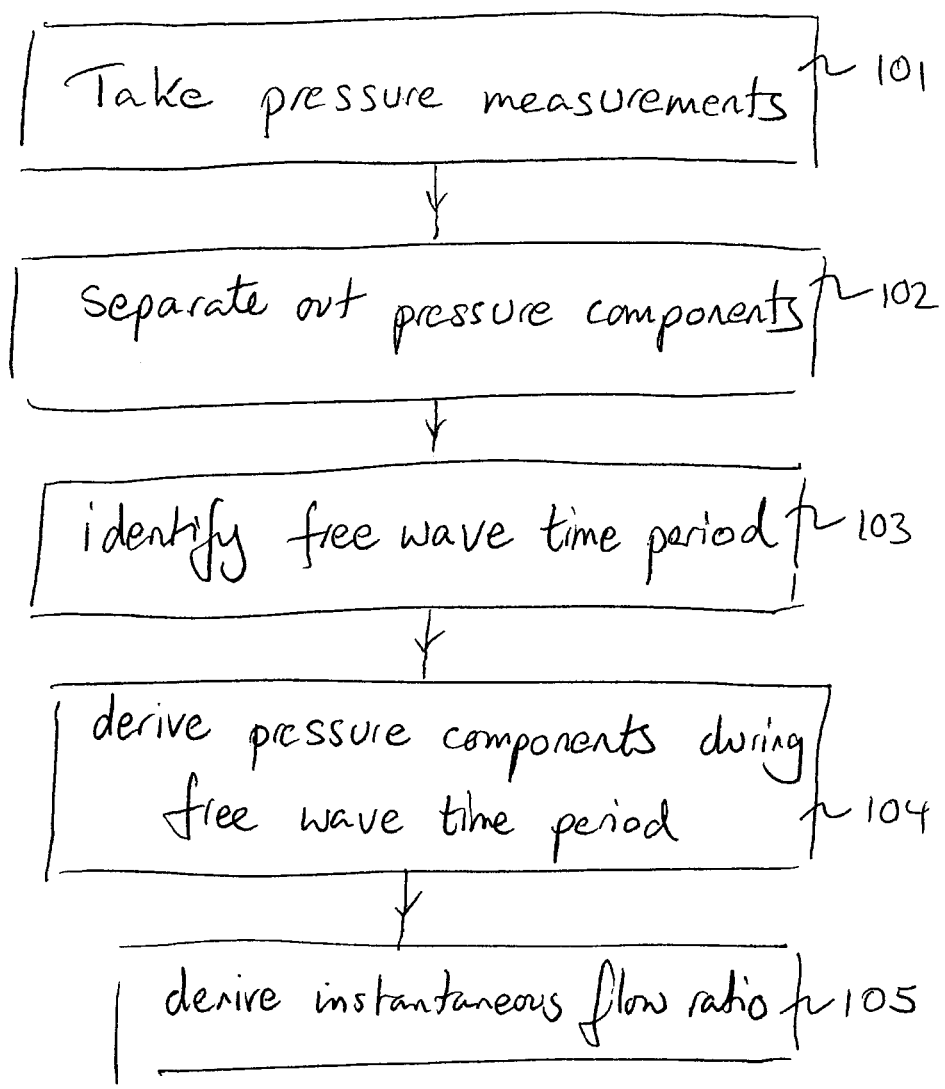
FIG. 3 is a flow diagram illustrating a method embodying the present invention.

Referring to FIG. 2, an apparatus 1 embodying the invention comprises a probe 2 such as an intra-arterial pressure wire (WaveWire or Combowire (Volcano Corp.) or Radi pressure wire (St Jude Medical) with a pressure measurement transducer 3—i.e. a device measuring pressure (P), and a processor 4 to analyse and operate on the pressure measurements. A signal line 5 relays the pressure measurement signal from the transducer 3 to the processor 4. The signal line 5 is illustrated both as a wired connection 5 and as a wireless connection 5'—either configuration is available.

The processor 4 operates on the pressure measurements received from the transducer 3 in accordance with a number of algorithms which are discussed in greater detail below. The apparatus 1 may be provided in the following configurations or combination of configurations, but these are not an exhaustive list of configurations:

i) a stand-alone device incorporating a probe with pressure measurement capacity in wired connection with a processor to provide on-device analysis;

ii) a device incorporating a probe with pressure measurement capacity in wireless connection with a processor to provide analysis at the processor;

iii) a stand-alone device incorporating a probe with pressure measurement capacity and a data storage device operable to record measurement data for real time or subsequent communication to a processor to provide analysis at the processor (real time and/or off-line); and iv) a device incorporating a probe with pressure measurement capacity in wireless connection with a data storage device operable to record measurement data for real time or subsequent communication to a processor to provide analysis at the processor (real time and/or off-line).

In the cardiac environment where the apparatus 1 is configured as part of haemodynamic equipment, the apparatus is configured using the processor 4 in the haemodynamic equipment, such as in McKesson equipment—Horizon Cardiology™, a cardiovascular information system (CVIS). Such configurations are particularly effective for the equipment processor to perform off-line analysis of the pressure data.

The apparatus 1 (and in particular the probe 2) can be used in combination with other haemodynamic equipment, medical imaging equipment and/or inpatient marker location equipment.

In a cyclic fluid flow system, there are time windows in which the rate of change of the fluid flow velocity tends to zero—i.e. dU tends to zero. At these times, termed here "wave free periods", it is possible to separate the wave pressure in the fluid at a measurement site into forward and backward pressures using the pressure waveform alone. This negates the need for measurement of flow velocity.

In a specific example of a cardiac cycle, at any point in the cardiac cycle $dP_+$ is determined by dP+ρc dU. dU is large during parts of the cardiac cycle when significant proportions of wave energy are present (i.e. during left ventricular contraction). However, there are times in the cardiac cycle when dU tends to zero. This can be a single moment or sample in time, or a multiple moments or samples in time. At such times, the dU term can be cancelled and $dP_+$ or $dP_-$ estimated using the dP term alone.

In accordance with this example of the invention, pressure samples are taken at or over the wave free period when dU tends to zero. Precise adherence to pressure sampling at or over the wave free period is not essential but pressure sampling does need to take place when the influence of dU is minimised and preferably when tending to zero.

At or over the wave free period when the influence of dU is minimised or negated entirely, the dU side is cancelled from the separated pressures so:

$dP_+$ is calculated as $$dP_+ = \frac{1}{2(dP + \rho c \, dU)}$$

and $dP_-$ is calculated as $$dP_- = \frac{1}{2(dP - \rho c \, dU)}$$

With the dU term cancelled) the separated pressures are calculated as:

$$dP_+ = \frac{1}{2}dP$$

and $$dP_- = \frac{1}{2}dP$$

When dU tends to zero, the dU side is cancelled from the solution and $dP_+$ is calculated as:

$$dP_+ = \frac{1}{2}dP$$

and $dP_-$ as, $$dP_- = \frac{1}{2}dP$$

The apparatus and method provide for the separation of the wave pressure in the fluid at a measurement site into forward and backward pressures using the pressure waveform alone dispensing with the need for any measurement of flow velocity. This advance allows use of technically simplified equipment which does not need to measure fluid flow velocity.

In the apparatus and method embodying the invention, the pressure measurements are made at baseline during the free wave period and not during hyperaemia. This is contrary to the teaching of FFR measurement in combined flow rate and pressure measurement apparatus where measurements are specifically taken at hyperaemia. This is because examples of the invention extract the forward pressure component, rather than (as in conventional FFR) having to minimise the contribution of backward pressure from the measured pressure by administration of vasodilators. If measurements are made during vasodilator hyperaemia, then measurements will not be reliable as dU increases significantly at this time.

Figure 4:
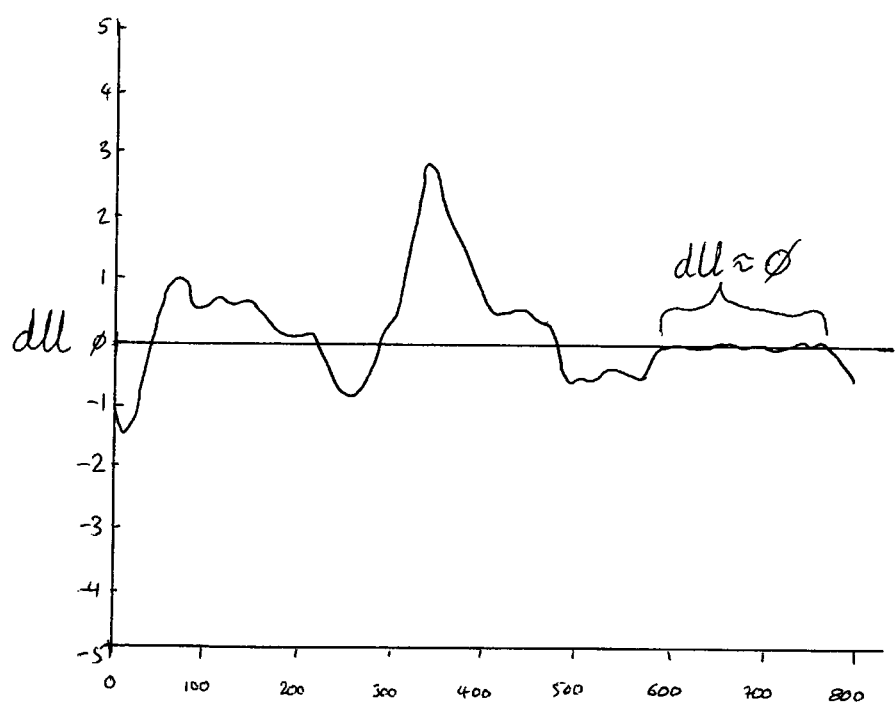
FIG. 4 shows an example of a free wave period in a cardiac environment, which free wave period is used in an apparatus and method embodying the present invention.

FIG. 4 shows an example of dU fluctuating over a cycle. There is an identifiable window where dU tends to zero (marked at 580 ms through to 770 ms in this example). The window is identified for example by being: heuristically learnt by the processor; linked to characteristics of the pressure waveform; or a certain time window after another event in the waveform e.g. starting at a predetermined time (250 ms) after event of $dU_{max}$ and lasting for a predetermined period (150 ms)—note $dU_{max}$ can be reliably observed from pressure measurements of the waveform. The wave free period is identifiable using online analysis in real time or can be identified using offline analysis.

For example, in a cardiac environment, detecting minimised dU (wave free period) from pressure measurements can be carried out as follows:

identify peak pressure time ($t_{Pmax}$)
identify end of pressure waveform time ($t_{Pend}$)
sample pressure measurements from $t_{Pmax}$ to $t_{Pend}$
analyse pressure measurements from ($t_{Pmax}$+150 ms) through to ($t_{Pend}$−50 ms)=wave free period.

Another example for identifying the wave free period is to base its identification on characteristics of the pressure waveform. This is advantageous because identification is not tied to fixed time points. In this specific example:

calculate the isolated forward (or backward) pressure ratio;
calculate standard deviation of isolated forward (or backward) pressure ratio
select the time period (free wave period) after peak pressure time point where the standard deviation is in the lowest 5% and if no points are identified, select the time period where the standard deviation is in the lowest 10% and so on.

The measurements are continuous within the identified free wave period and/or for a period of at least ~=100 ms.

Another example for identifying the free wave period is:
identify the peak pressure time point;
identify the end of the pressure waveform time point; and
specifying the free wave period as a predetermined portion mid-window between these two time points. Preferably, the free wave period is identified as the mid 3/5 window between these two time points.

In the cardiac environment, reliable measurements are taken in the window where dU varies less than $+/-2\times10^{-4}$ from the zero crossing, where $dU_{max}$, is $3\times10^{-3}$, where dU is 20% or less of $dU_{max}$, preferably 10% or less, most preferably 5% or less. dU oscillates around the mean over the wave free period so its net contribution to separated pressures (i.e. $P_+$) is minimised as the −ve contributions cancel the +ve contributions. The oscillations about the mean during the wave free period (the time window) in a cardiac environment are due to limitations in the measurement equipment which will not detect small changes accurately.

Further this advance provides a measure of the severity of a constriction using the measure of isolated pressure ratio.

Further this advance negates the need in the cardiac environment for the administration of potent vasodilators.

There are particular needs in the cardiac environment for simplified equipment having the smallest possible footprint (or being the least invasive requiring the smallest possible entry site) so the provision of an isolated pressure ratio measurement device or probe which has only one measurement device mounted on or in the probe represents a significant technical advance in that field.

Further, such devices or probes in the cardiac field include signal lines from the probe which terminate either in a transmitter for relaying the measurement signal to a processor or a processor itself. If there is a flow sensor and a pressure sensor, then two different measurement devices are in/on the same probe and there are also two signal lines required to take the signal from the two distinct measurement devices. The loss, in examples of the invention, of the flow sensor from the system is extremely beneficial as it reduces the complexity of the device, can improve handling of the probe and can reduce the number of signal lines necessary to take the measurement signal(s) away from the measurement devices. In the case of examples of the invention, there is only one measurement device—that of pressure measurement and the need for a flow sensor in addition to one or more pressure sensors is obviated. A single pressure sensor wire can be more manoeuvrable than a wire with both pressure and flow sensors. Having a flow sensor in addition to the pressure sensor is sub-optimal for guide wire design.

Pressure-only measurements are taken relative to the constriction. Multiple measurements can be taken in preference to one measurement. The probe 2 can be moved relative to the constriction, in which case, multiple measurements would be taken.

There is a further sophistication to the above described apparatus and method which concerns the identification of wave free periods—those times in the cyclic flow when dU tends to zero. A person skilled in the art is able to calculate and identify wave free periods—occurring as they do during periods of the cardiac cycle when wave activity is minimised or absent.

For a given wave free period from time point $tw_0$ to time point $tw_1$: with $P_+$ (during any wave free period $tw_0$ to $tw_1$) as, $$P_+ = \int_{tw0}^{tw1} dP_+$$

and $P_-$ as, $$P_- = \int_{tw0}^{tw1} dP_-$$

where $P_{+proximal}$ is defined as, $$P_{+proximal} = \int_{tw0}^{tw1} dP_{+proximal}$$

and $P_{+distal}$ is defined as, $$P_{+distal} = \int_{tw0}^{tw1} dP_{+distal}$$

and $P_{-proximal}$ is defined as, $$P_{-proximal} = \int_{tw0}^{tw1} dP_{\times proximal}$$

and $P_{-distal}$ is defined as, $$P_{-distal} = \int_{tw0}^{tw1} dP_{-distal}$$

The isolated pressure ratio using separated pressures is thus isolated forward pressure:

$$\frac{P_{+\ distal}}{P_{+\ proximal}}$$

Or isolated backward pressure, $$\frac{P_{-\ distal}}{P_{-\ proximal}}$$

Calculating the isolated pressure ratio using this technique over the wave free period gives a pressure-only assessment of the severity of the constriction, such as a stenosis. There is no need to provide flow velocity measurement equipment on the probe 2 in addition to the pressure measurement transducer 3 and there is no need to process any flow velocity measurement.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A method of assessing a narrowing in a fluid filled tube having a fluid flow pressure wave having a backward-originating pressure component and a forward-originating pressure component without taking a flow velocity measurement, comprising:
    taking pressure measurements in the tube using a pressure measurement device;
    separating, using a processing system, the pressure components into the backward-originating pressure component and the forward-originating pressure component;
    identifying, using the processing system, a time window when the differential of flow velocity (dU) is minimal or absent; and
    deriving, using the processing system, the backward and forward pressure components for pressure measurements taken in at least the time window.

2. The method of claim 1, further comprising deriving the backward and forward pressure components during the time window.

3. The method of claim 1, wherein the time window is from time point $tw_0$ to time point $tw_1$ and the forward-originating pressure component ($P_+$) is:

$$P_+ = \int_{tw0}^{tw1} dP_+$$

and the backward-originating pressure component ($P_-$) is:

$$P_- = \int_{tw0}^{tw1} dP_-.$$

4. The method of claim 3, wherein the isolated pressure ratio provides an assessment of the severity of the constriction, wherein the isolated forward pressure ratio is:

$$\frac{P_{+\ distal}}{P_{+\ proximal}}$$

and the isolated backward pressure ratio is:

$$\frac{P-\text{distal}}{P-\text{proximal}}.$$

5. The method of claim 1, wherein the time window is identified by analysing a characteristic of the pressure waveform.

6. The method of claim 1, wherein the time window is identified as starting at a predetermined time after an identifiable event and lasting for: a predetermined period after the event; or a predetermined period before or after a further event.

7. The method of claim 6, wherein the identifiable event is a peak pressure event and the further event is an end of pressure waveform event.

8. The method of claim 1, wherein the time window is a period in which dU fluctuates around a zero crossing.

9. The method of claim 1, wherein the time window is a period in which dU is 20% or less, 10% or less, or 5% or less of $dU_{max}$.

10. The method of claim 1, wherein a wave free period is identified as the time period in which the standard deviation of isolated forward (or backward) pressure ratio after a peak pressure time point is below a predetermined percentage.

11. The method of claim 1, wherein a wave free period is identified by:
  identifying a peak pressure time point;
  identifying the end of the pressure waveform time point; and
  specifying the free wave period as a predetermined portion mid-window between these two time points.

12. An apparatus to assess a narrowing in a fluid filled tube having a fluid flow pressure wave having a backward-originating pressure component and a forward-originating pressure component without taking a flow velocity measurement, the apparatus comprising:
  a pressure measurement device operable to take pressure measurements in the tube; and
  a processor operable to separate the pressure components into the backward-originating pressure component and the forward-originating pressure component; identify a time window when the differential of flow velocity (dU) is minimal or absent; and to derive the backward and forward pressure components for pressure measurements taken in at least the time window.

13. The apparatus of claim 12, wherein the processor further derives the backward and forward pressure components during the time window.

14. The apparatus of claim 12, wherein the processor further identifies the time window.

15. The apparatus of claim 12, further comprising a signal line between the pressure measurement device and the processor.

16. The apparatus of claim 15, wherein the signal line is a wired connection between the pressure measurement device and the processor; OR wherein the signal line is a wireless connection between the pressure measurement device and the processor.

17. The apparatus of claim 16, wherein the pressure measurement device relays the pressure measurements to a data storage device which stores the pressure measurements and is remote from the processor.

18. An apparatus comprising:
  a processor configured to assess a narrowing in a fluid filled tube having a fluid flow pressure wave having a backward-originating pressure component and a forward originating pressure component without taking a flow velocity measurement, the processor:
  analysing pressure measurements taken in a tube;
  separating the pressure components into the backward-originating pressure component and the forward-originating pressure component;
  identifying a time window when the differential of flow velocity (dU) is minimal or absent; and
  deriving the backward and forward pressure components for pressure measurements taken in at least the time window.

19. A non-transitory computer readable medium containing computer instructions stored therein for causing a computer processor to assess a narrowing in a fluid filled tube having a fluid flow pressure wave having a backward-originating pressure component and a forward-originating pressure component without taking a flow velocity measurement, the instructions comprising:
  analysing pressure measurements taken in a tube;
  separating the pressure components into the backward-originating pressure component and the forward-originating pressure component;
  identifying a time window when the differential of flow velocity (dU) is minimal or absent; and
  deriving the backward and forward pressure components for pressure measurements taken in at least the time window.

* * * * *